United States Patent [19]
Doukas

[11] Patent Number: 6,121,320
[45] Date of Patent: *Sep. 19, 2000

[54] COMBINATION ANTI-LEUKEMIC THERAPY BY UTILIZING SURAMIN AND BIOLOGIC RESPONSE MODIFIERS

[75] Inventor: Michael A. Doukas, Lexington, Ky.

[73] Assignee: The University of Kentucky Research Foundation, Lexington, Ky.

[*] Notice: This patent issued on a continued prosecution application filed under 37 CFR 1.53(d), and is subject to the twenty year patent term provisions of 35 U.S.C. 154(a)(2).

[21] Appl. No.: 09/031,037

[22] Filed: Feb. 26, 1998

Related U.S. Application Data

[60] Provisional application No. 60/039,260, Feb. 26, 1997.

[51] Int. Cl.$^7$ ........................ A61K 31/20; A61K 31/185; A61K 31/17
[52] U.S. Cl. .......................... 514/559; 514/560; 514/577; 514/597
[58] Field of Search ................................... 514/559, 560, 514/597, 577, 547

[56] References Cited

U.S. PATENT DOCUMENTS

| | | | |
|---|---|---|---|
| 4,232,150 | 11/1980 | Nair et al. | 536/119 |
| 4,266,077 | 5/1981 | Conrow et al. | 562/427 |
| 4,304,903 | 12/1981 | Nair et al. | 536/4 |
| 4,371,524 | 2/1983 | Shinohara et al. | 536/4 |
| 4,387,059 | 6/1983 | Conrow et al. | 260/506 |
| 4,393,055 | 7/1983 | Nair et al. | 536/8 |
| 4,407,796 | 10/1983 | Miner et al. | 536/4.1 |
| 4,414,207 | 11/1983 | Nair et al. | 536/8 |
| 4,459,293 | 7/1984 | Miner et al. | 536/4.1 |
| 4,591,604 | 5/1986 | Conrow et al. | 514/557 |
| 5,158,940 | 10/1992 | LaRocca et al. | 514/54 |
| 5,585,243 | 12/1996 | Aster et al. | 435/7.21 |

OTHER PUBLICATIONS

R. Lopez et al., "The Synergistic and Antagonistic Effects of Cytotoxic and Biological Agents on the In Vitro Antitumour Effects of Suramin", *European Journal of Cancer*, vol. 30A, No. 10, 1994, pp. 1545–1549.

A. Falcone et al., "Synergistic Antiproliferative Activity of Suramin and α2A–Interferon Against Human Colorectal Adenocarcinoma Cell Lines: In vitro Studies", *European Journal of Cancer*, vol. 30A, No. 4, 1994, pp. 516–520.

Michael Doukas et al., "Inhibition of granulocyte–macrophage colony–stimulating factor (GM–CSF) activity by suramin and suramin analogs is correlated to interaction with the GM–CSF nucleotide–binding site", 21284q, *Chemical Abstracts 1 –Pharmacology*, vol. 124, No. 3, 1996, p. 57. Abstract Only.

Emmanuel Roilides et al., "Suppression of polymorphonuclear leukocyte bactericidal activity by suramin", 204843s, *Chemical Abstracts*, vol. 118, 1993, p. 36. Abstract Only.

Krystyna Gnacinska et al., "Block of the macrophage system and blood lipids", 88004n, *1–Pharmacodynamics*, vol. 92, 1980, p. 35. Abstract Only.

V. Dimov et al., "Phagocytic and candidacidal activity of alveolar macrophages from suramin–treated mice", 48367f, *Chemical Abstracts,* vol. 101, 1984, pp. 38. Abstract Only.

P. Draper, "Effects of anionic inhibitors of phagosome–lysosome fusion in cultured macrophages when the ingested organism is *Mycobacterium lepraemurium*", 54457b, *Chemical Abstracts*, vol. 91, 1997, p. 506. Abstract Only.

Edward L. Pesanti, "Suramin effects on macrophage phagolysosome formation and antimicrobial activity", 84580n, *Chemical Abstracts*, vol. 89, 1978, p. 16. Abstract Only.

V. Dimov et al., "Influence of suramin and cyclophoshamide administered in combination on alveolar macrophages", 185492m, *Chemical Abstracts*, vol. 100, 1984, p. 34. Abstract Only.

M. K. Pratten, "Effect of suramin on pinocytosis by resident rate peritoneal macrophages: an analysis using four difference substrates", 114605q, *Chemical Abstracts*, vol. 100, 1984, p. 22. Abstract Only.

Glenn A. Warr et al., "Lung macrophage defense responses during suramin–induced lysosomal dysfunction", 215t, *1–Pharmacology*, vol. 99, 1983, p. 221. Abstract Only.

Hong Xiang Zhang et al., "Modulation by suramin of NK and monocytic cell–mediated cytotoxicity in human and murine cells", 221980r, *Chemical Abstracts*, vol. 109, 1998, pp. 24–25. Abstract Only.

S. Trifonov, et al., "Activation of chicken peritoneal macrophages by suramin", 198002s, *1–Pharmacology*, vol. 108, 1988, p. 33. Abstract Only.

R. Toshkova et al., "Immunoprotective and immunomodulating activities of suramin in hamsters with myeloid tumor, induced by Graffi virus", 246203s, *Chemical Abstracts*, vol. 23, 1995, p. 42. Abstract Only.

C. Schiller et al., "Influence of suramin on the expression of Fc receptors and other markers on human monocytes and U937 cells, and on their phagocytic properties", 99107s, *1–Pharmacology*, vol. 121, 1994, pp. 27–28. Abstract Only.

R. LaRocca et al., "Use of suramin to treat rheumatologic diseases", 64775g, *1–Pharmacology*, vol. 115, 1991, p. 101. Abstract Only.

P. Novales–Li, "In vitro immunopharmacologic effect of suramin on modifying Th–subset cytokine levels in splenocytes and T–cell clones: a therapeutic application for autoimmune disease", 158032w, *Chemical Abstracts 1–Pharmacology*, vol. 125, No. 13, 1996, p. 68 Abstract Only.

(List continued on next page.)

*Primary Examiner*—Jerome D. Goldberg
*Attorney, Agent, or Firm*—McDermott, Will & Emery

[57] ABSTRACT

A method of treating leukemia which includes administering an effective amount of composition comprising suramin and a biological response modifier, wherein the suramin and the biological response modifier show synergistic or additive anti-leukemic activity. A pharmaceutical composition is also disclosed.

14 Claims, 8 Drawing Sheets

OTHER PUBLICATIONS

M Doukas et al., "Suramin and suramin analog activity against leukemic cell lines: Correlation to interaction with the granulocyte/macrophage colony stimulating factor nucleotide–binding site", Experimental Therapeutics #2037, *Proceedings of the American Association for Cancer Research*, vol. 37, Mar. 1996, pp. 299–300. Abstract Only.

Nakashima et al., Med. Microbiol. Immunol., 176(4), 189–98 Abstract Only 1987.

Breitman et al., Proc. Natl. Acad. Sci. U.S.A., 77950, 2936–40 Abstract Only 1980.

Doukas et al., #2036, Proc. Am. Assoc. for Cancer Research, vol. 37 Mar. 1996.

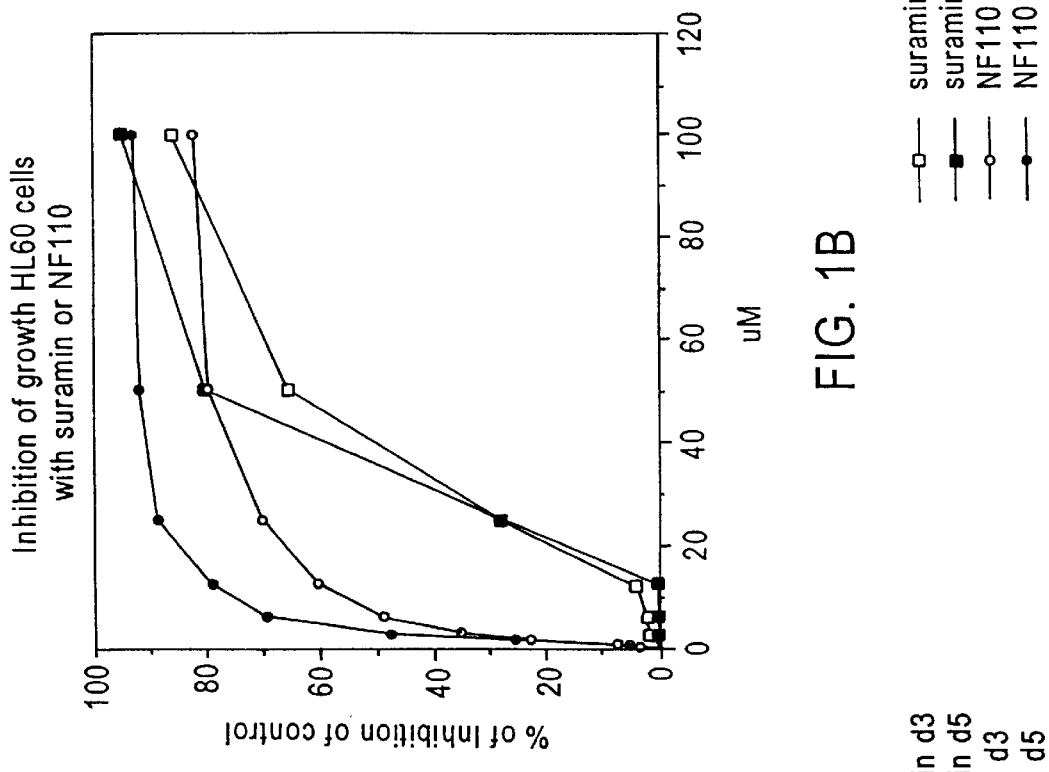
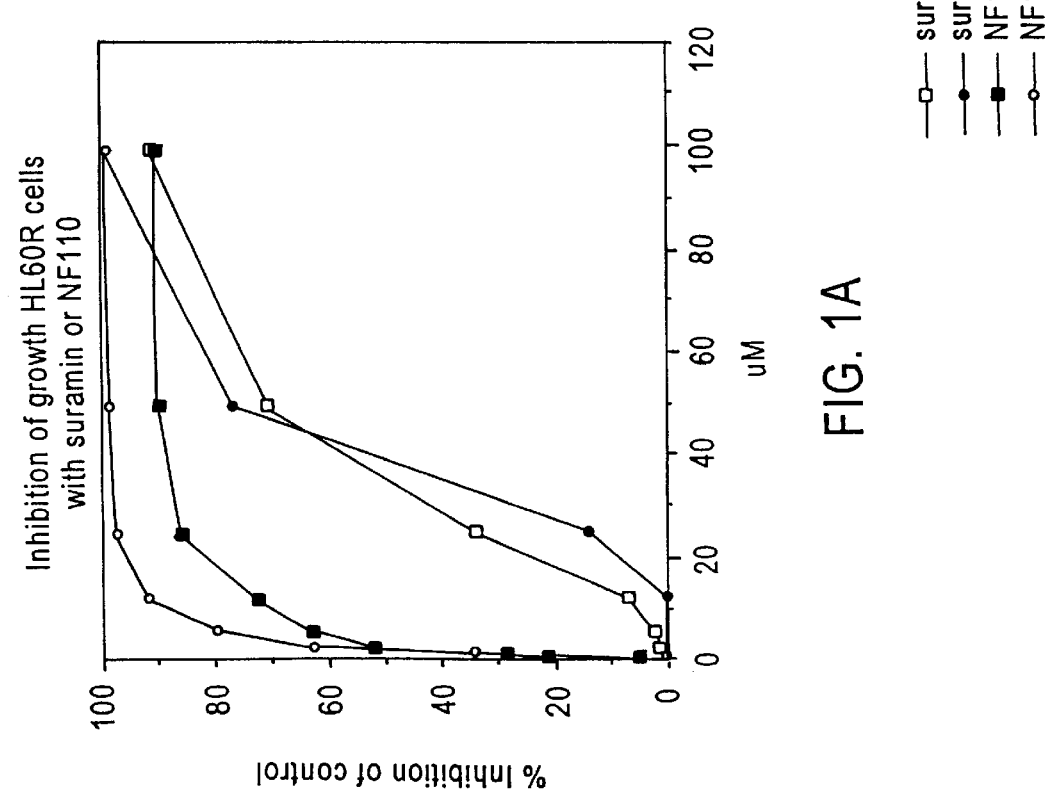

COMBINATION ANTI-LEUKEMIC THERAPY BY UTILIZING SURAMIN AND BIOLOGIC RESPONSE MODIFIERS

RELATED APPLICATIONS

This application claims priority from provisional patent application Ser. No. 60/039,260, filed Feb. 26, 1997 entitled "COMBINATION ANTI-LEUKEMIC THERAPY BY UTILIZING SURAMIN AND BIOLOGIC RESPONSE MODIFIERS", which is incorporated herein by reference.

TECHNICAL FIELD

The present invention relates to a combination of anti-leukemic therapy utilizing suramin and biological response modifiers. The anti-growth factor suramin is used in combination with several different biologic response modifying agents such as all-trans retinoic acid (ATRA) and interferon-α. Synergistic activity between the compositions was shown with these therapies.

BACKGROUND ART

U.S. Pat. No. 5,158,940 to LaRocca et al., issued Oct. 27, 1992. This patent discloses in col. 1 and col. 2 that suramin, a polysulfonated napthtylurea has a demonstrated ability to inhibit the activity of various growth factors in vivo. Suramin is known to treat rheumatoid arthritis and related diseases. The '940 patent discloses the usefulness of suramin against autoimmune and allergenic diseases such as Crohn's disease, ulcerative colitis, sarcoidosis, rheumatoid arthritis, scleroderma, polyarteritis, psoriasis, interstitial and glomerular nephrites, systemic lupus erythematosus, polymyositis, Sjogren's syndrome, asthma and other inflammatory alveolar disorders.

U.S. Pat. No. 4,591,604 discloses a method of inhibiting the complement system by administering multisulfonated naphthalene ureas (see col. 6, line 7).

U.S. Pat. No. 4,459,293 discloses a method of modulating the complement system by administering arylene sulfate derivatives and their cation salts.

U.S. Pat. No. 4,414,207 discloses sulfate and salts thereof and their use as inhibitors of the complement system. The complement system is stated in col. 1, lines 39 to 46 to play an important role as a mediator of immune, allergic, immunochemical and/or immunochemical and/or immunopathological reactions. Col. 3, line 45 indicates that suramin compounds are known for inhibiting the complement system.

U.S. Pat. No. 4,407,796 discloses modulators of the complement system and describes in col. 6, line 10 that suramin sodium is known for the treatment of hereditary and angioneurotic edema.

U.S. Pat. No. 4,393,055 discloses in sulfate derivatives and their use as complement inhibitors. Col. 4, line 64 describes that suramin sodium is useful in the treatment of hereditary angioneurotic edema.

U.S. Pat. No. 4,387,059 discloses 6-naphthalenetri-sulfonic acid salts. Col. 4, line 57 describes that suramin sodium is known for the treatment of hereditary angioneurotic edema.

U.S. Pat. No. 4,371,524, discloses anti-complementary agents comprising soyasapogenol B compounds. Col. 4, line 17 discloses that suramin sodium is known as a complement inhibitor.

U.S. Pat. No. 4,304,903, discloses at col. 3, line 37 that suramin is known as a complement inhibitor.

U.S. Pat. No. 4,266,077, discloses at col. 3, line 23 that suramin is known as a complement inhibitor.

U.S. Pat. No. 4,232,150, discloses at col. 5, line 16 that suramin sodium is known for the treatment of hereditary angioneurotic edema.

U.S. Pat. No. 5,585,243, discloses at col. 10, line 34 that suramin sodium causes antibody dependent drug-induced thrombocytopenia.

Chemical Abstracts Vol. 124, No. 3, Abstract No. 21284q, published in 1996 discloses the inhibition of granulocyte-macrophage colony-stimulating factor activity by suramin and suramin analogs. This action is correlated to interaction with the GM-CSF nucleotide-binding site. This publication has a publication date of 1995.

Chemical Abstracts Vol. 118, No. 21, Abstract No. 204843s, published in 1996 describes the suppression of polymorphonuclear leukocyte bactericidal activity by suramin.

Chemical Abstracts Vol. 92, No. 11, Abstract No. 88004n, published in 1980 describes blockage of the macrophage system and blood lipids with suramin.

Chemical Abstracts Vol. 97, No. 7, Abstract No. 54457b with a publication date of 1979. This publication describes the effect of suramin on phago-lysosome formation by poly-glutamic in mycobacterium infection.

Chemical Abstracts Vol. 89, No. 11, Abstract No. 84580n, published in 1978. This publication describes suramin effects on macrophage phagolysosome formation and antimicrobial activity.

Chemical Abstracts Vol. 101, No. 7, Abstract No. 48367f, published in 1984 describes phagocytic and candidacidal activity on alveolar macrophages from suramin-treated mice. Chemical Abstracts Vol. 100, No. 23, Abstract No. 185492m, 1984, describes the influence of suramin and cyclophosphamide administered in combination on alveolar macrophages.

Chemical Abstracts Vol. 100, No. 15, Abstract No. 114605q, 1984, describes the effect of suramin on pinocytosis by rat peritoneal macrophages.

Chemical Abstracts Vol. 99, No. 1, Abstract No. 215t, 1993 describes the lung macrophage defense responses during suramin-induced lysomal dysfunction.

Chemical Abstracts Vol. 109, No. 25, Abstract No. 221980r, 1988, describes the modulation by suramin of NK and monocytic cell-mediated cytotoxicity in human and murine cells.

Chemical Abstracts Vol. 108, No. 23, Abstract No. 198002s, 1988, describes the activation of chicken peritoneal macrophages by suramin.

Chemical Abstracts Vol. 123, No. 19, Abstract No. 246203s, 1995, describes the immunoprotective and immunological activities of suramin in hamsters with myeloid tumor.

Chemical Abstracts Vol. 121, No. 9, Abstract No. 99107s, 1994, describes the influence of suramin on the expression of Fc receptors and other markers of human monocytes and U937 cells.

Chemical Abstracts Vol. 115, No. 7, Abstract No. 64775g, describes the use of suramin to treat rheumotologic diseases.

Chemical Abstracts Vol. 125, No. 13, Abstract No. 158032w, describes the immunopharmalogical effect of suramin on modifying TH subset cytokine levels in spleencites and T-cell clones. Also describes as a therapeutic application for autoimmune disease.

Abstract published Mar. 1, 1996 by Doukas et al. discloses that all-trans retinoic acid (ATRA) and suramin had synergistic activity in interrupting autocrine driven leukemic cell growth.

Lopez et al., *European Journal of Cancer Research*, The Synergistic and Antagonistic Effects of Cytotoxic and Biological agents on the In Vitro Antitumor Effects of Suramin, Vol. 30A, No. 10, pp. 1545–1549, (1994) discloses that suramin and α-interferon and γ-interferon did not have synergistic activity against PL-3 tumor cell line.

There is a need in the art for new leukemia treatments. The present invention overcomes deficiencies of prior art leukemia treatments.

DISCLOSURE OF THE INVENTION

The present invention relates to a method of treating leukemia comprising administering an effective amount of composition comprising suramin and a biological response modifier. In a preferred embodiment, said suramin and said biological response modifier show synergistic anti-leukemic activity.

In a preferred embodiment the biologic response modifier is selected from the group consisting of all-trans retinoic acid (ATRA), α-interferon γ-interferon, vitamin D, 9-cis-retinoic acid, cytosine arabinoside, adriamycin, mitoxantrone, VP-16, idarubicin and tumor necrosis factor.

The invention also relates to a pharmaceutical composition comprising suramin and a biological response modifier. In the composition the suramin and the biological response modifier show synergistic anti-leukemic activity.

In a preferred embodiment the biologic response modifier is selected from the group consisting of all-trans retinoic acid (ATRA), interferon-α, γ-interferon, vitamin D, 9-cis-retinoic acid, cytosine arabinoside, adriamycin, mitoxantrone, VP-16, idarubicin and tumor necrosis factor.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF DRAWINGS

FIGS. 1A and 1B show HL60 leukemia cell proliferation after administration with suramin and α-interferon.

DESCRIPTION OF THE INVENTION

Figure 2:
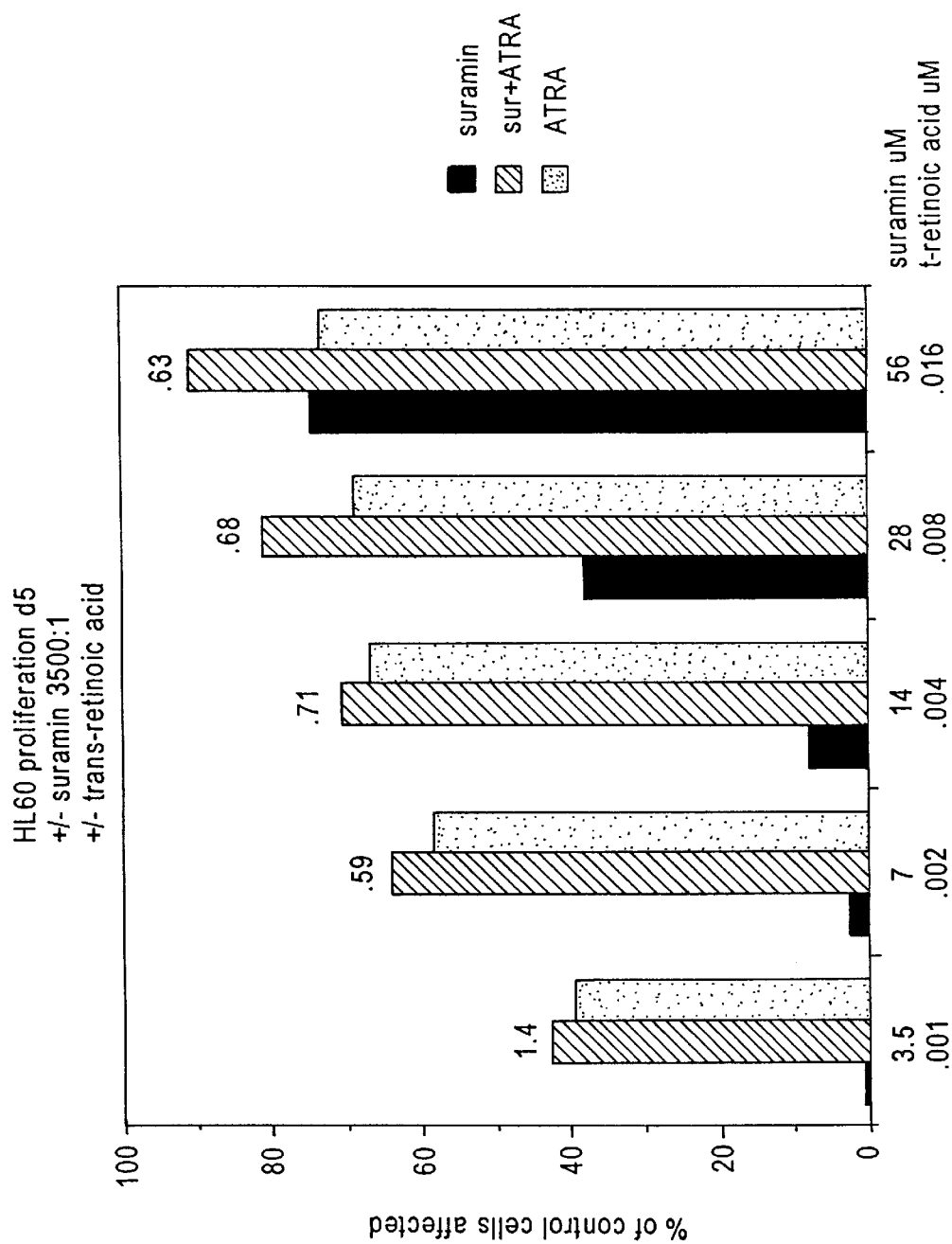
FIG. 2 shows suramin plus ATRA strongly inhibited HL-60 and HL-60R growth. Analysis utilizing a software program reveals that this activity is a truly synergistic one.

Retinoid compounds (vitamin A derivatives) when used in conjunction with pharmacologic antigrowth factor agents (suramin and analogs) can result in synergistic activities against myeloid leukemias. Objectives of the invention include in vitro testing using human leukemic cell lines derived from patients with acute promyelocytic leukemia (NB4) and acute myeloid leukemia (HL-60) to first ascertain the most advantageous combinations to inhibit these leukemia cell lines. Compounds tested include all-trans retinoic acid (ATRA), in combination with suramin or its most potent analog, NF110. Other analogues include NF032, NF201, NF023, NF103 and the class of compounds known as azo dyes.

The invention allows for a treatment of leukemia and expands the use of retinoids into other forms of leukemia other than acute promyelocytic leukemia, which is the form of leukemia which has seen the greatest usefulness of retinoids. This is directly relevant to the role of vitamin nutrients in the treatment of certain malignancies, in this case leukemias, and allows for treatment of malignancy by drugs with better activity and which do not have the side effects of standard chemotherapy.

The retinoids are vitamin A analogs that play a critical role in normal differentiation and growth (1). The oxidized form of vitamin A is important in maintaining epithelial cellular integrity (2). Retinoid therapy of some hematopoietic and non-hematopoietic models inhibits carcinogenesis (3). The greatest therapeutic triumph of retinoid analogs rests with the use of all-trans retinoic acid (ATRA) in acute promyelocytic leukemia (APL) (4). This compound stimulates the clonal growth of normal hematopoietic progenitors yet inhibits the growth of HL-60 and NB4 cells (acute myeloid and acute promyelocytic leukemia cell lines, respectively) (5). Its usage as a single agent results in complete remission rates in APL of 70% or better (4,6). The remarkable activity of ATRA in this particular leukemia is known to correspond to the specific chromosomal translocation t (15,17) which results in the fusion product, PML/RARa (promyelocytic leukemia/retinoic acid receptor-a). The PML/RARa chimeric protein appears to function as a "dominant-negative" retinoid receptor, thus blocking the normal maturation of promyelocytes (7). The precise function of PML/RARa is being intensively studied, and it appears that, ATRA clinically restores the capacity of APL cells to terminally differentiate with resultant apoptosis and hence disappearance of leukemic blasts.

This maturation process of APL cells is associated with the "ATRA syndrome" in a subset of patients (5–20%) reported. This is characterized by fever, respiratory distress and chest x-ray abnormalities, and weight gain (4). Several important caveats of ATRA responses in APL are critical in the long-term prognosis. First, ATRA remissions are brief (8). This is an interesting phenomenon and may relate to altered pharmacokinetics with prolonged therapy (9) or to the development of intrinsic cellular resistance (10). A proportion of patients (60%) may enjoy long term remissions when ATRA treatment is followed by chemotherapy (6). However, 30–40% of patients are either resistant to ATRA at diagnosis or relapse, and are thus unlikely of being cured by conventional therapy. Other clinical oncology trials of retinoids include their use (13-cis retinoic acid or ATRA) in the myelodysplastic syndrome with mixed results (11,12), in chronic myelogenous leukemia (vitamin A) with a significant improvement in overall survival when used in conjunction with chemotherapy (6), and pilot trials (13-cis retinoic acid) in cervical cancer used in conjunction with interferon-α (13,14). The combination trials are accompanied by some in vitro laboratory data which indicate that retinoids may have efficacy if used in combination with appropriately chosen agents that render not additive, but rather synergistic activity (15).

One such combination approach involving retinoids, which down-regulate certain cytokine receptors on tumor cells, coupled with antigrowth factor agents which block cytokine-receptor interaction and hence both work to interrupt malignant cell autocrine growth factor loops (16). Such autocrine mechanisms exist in leukemias (and certain solid tumors) and would be a novel approach to improving cure rates in APL therapy and reduce the incidence of the development of resistance which has been correlated with new leukemia cell cytokine production (17). Appropriate combination therapies may also be useful in expanding retinoid efficacy in other leukemias in which autocrine growth mechanisms have been proposed.

Granulocyte/macrophage-colony stimulating factor (GM-CSF) is a cytokine which has a broad range of proliferative, differentiating, and activating effects upon inflammatory cells and their precursors (18,19). Recent work in our laboratories has resulted in the description of previously unknown nucleotide binding interactions with several cytokines, specifically interleukin (IL)-2 (20), interleukin-1 (21), acidic FGF (22), and GM-CSF (23). The nucleotide binding site for GM-CSF appears by virtue of saturation and competitive binding studies to have specificity for adenosine nucleotide probes. Our work has revealed that the antigrowth factor agent suramin strongly interacts with this binding site (24) and our data support our hypothesis that this interaction may be central to its inhibitory activity on cellular proliferation.

Suramin's history dates to the early German organic chemical industry (25) and the discovery that it was an active antitrypanosomal agent (26). Hawking noted that the drug could bind to and inhibit many enzymes without an apparent underlying unifying theme (27). Interest sharpened with the discovery of inhibition of reverse transcriptase and several growth factors, the latter leading to clinical trials in prostate cancer (28). Growth factors (cytokines) have been shown to act as autocrine stimulators of a variety of normal hematopoietic cell types and acute leukemias (2931). Subsequent research proceeded on the hope that certain malignant tumors would be more sensitive than normal tissues (28).

An important, perhaps central, feature of suramin is its capacity to interfere with cytokine-receptor binding. In the class of hematopoietic cytokines, IL-2 and IL-6, share this effect (32,33). The precise mechanism is controversial with conflicting reports of altered cytokine quaternary structure with changes of deoligomerization (TNF-a) on the one hand (34), and aggregation (FGF and PDGF) on the other (35). Other activities upon a wide variety of cellular enzymes have been described (36–40) and, paradoxically in relation to its anti-growth factor action, an increase in protein tyrosine phosphorylation has been reported (41). It should be noted however that all of these studies involved cell culture and not isolated enzyme systems; the mechanism and pathways by which suramin affected each of these enzymes is unclear. In sum, the antigrowth factor activity via cytokine-receptor blockade, which agrees with our data on GM-CSF, appears to be a constant theme across multiple cytokines.

In spite of the demonstrated autocrine growth promoting role of cytokines such as GM-CSF and IL-1 in leukemia (31, 42–45), little work has been published with suramin's use for hematopoietic malignancies. In one study, five of nine evaluable follicular lymphoma patients achieved a partial remission of their disease with suramin (46). However, with the exception of four patients with agnogenic myeloid metaplasia (a chronic myeloproliferative disorder) (47), MEDLINE search revealed no suramin trials in myeloid leukemia. Suramin does strongly suppress in vitro the proliferation of the HL-60 acute leukemic cell line (48) and the work of Orchard (49) agrees with our finding of suramin inhibition of GM-CSF dependent cell growth (24).

Autocrine growth factor loops involving cytokines have been implicated as important in the growth of certain tumors and leukemias. The work of the inventors has shown that suramin is a potent agent against leukemic cells in vivo and has been expanded to include several suramin analogs. Due to the toxicities of suramin, the effectiveness of suramin used in combination with biologic agents specifically, all trans-retinoic acid (ATRA) has been studied. The goal was to ascertain if such combinations are merely additive or are synergistic.

All trans-retinoic acid has been found to be an effective agent for induction of remission when used as a single agent in acute promyelocytic leukemia and other retinoids are under study both as maintenance agents in acute leukemia and in other solid tumors. The possibility that such combinations are synergistic assists in dosing patients with suramin at levels which are less toxic and yet result in greater activity.

Cell lines which have been selected for ATRA resistance are utilized to examine if synergism remains or is abrogated with these retinoid resistant cell lines. Cell lines chosen for this study include the ATRA sensitive human acute leukemia HL-60 and ATRA sensitive APL line, NB4, both of which have been extensively studied. An ATRA resistant sub clone, HL-60R was obtained from Dr. Steve Collins. While originally described as an acute promyelocytic cell line, more recent work categorizes this line as an acute myelogenous leukemia. Therefore, a second ATRA resistant line (NB4.306) which is derived from the NB4 cell line from a patient with acute promyelocytic leukemia was obtained. The NB4tNB4.306 lines contain the t(lS,17) typical of APL.

The sensitivity of these cell lines to ATRA and suramin (or NF110) as single agents is assessed. ATRA dose response curves (10-5–10-9M) are generated as are suramin/analogue dose response curves (10-4–10-8M). These data for each individual cell line allow description of describe IC50 concentrations for the individual agents, and in the case of suramin analogues, permit comparison of efficacy.

Assays of proliferation consist of cell proliferation (3H-thymidine) assay as previously described or the MTT assay after 3–5 days of exposure to the agents. Cell proliferation is assayed using a modification of the original MTT calorimetric assay described by Mosmann (53). To better delineate the issues of proliferation (and inhibition thereof) versus differentiation, which is induced by certain of the agents being proposed for testing, an alternative method would utilize simple cell counting (Courter, Inc.) of aliquots at 3 and 5 days of continuous exposure with concomitant analysis of induced differentiation by cell morphology (NBT-positive) conducted. The percentage of differentiated cells in liquid culture determined by the NBT reduction test (as described, (54) allows for an estimate of the total number of cells which are still blast cells and therefore considered capable of continued leukemogenic growth. The most promising combinations are used to examine de novo acute myeloid leukemia patient samples in like fashion.

A SCID mouse host system is utilized and the most promising agent combinations are examined to determine the response of human leukemic cell lines in these host animals. Finally, the potential mechanisms of the ATRA/suramin synergistic activity as it relates to cytokine receptor density on treated human leukemia cell lines is examined.

Mechanisms of action and clinically relevant studies with retinoids in combination with antigrowth factor agents to improve the therapeutic index or expand the use of retinoids into other myeloid leukemias other than acute promyelocytic leukemia.

The work has direct relevance to the role of vitamin nutrients in the treatment of selected malignancies, in this case myeloid leukemias, and broadens the applications of retinoids by proving the theoretical unexpected advantage of combination usage with antigrowth factor agents.

The antigrowth factor activity of suramin was tested alone and in combination with all-trans retinoic acid (ATRA) against the human leukemic line HL-60 or its ATRA resistant subclone, HL-60R, to assess if an agent with the ability to interrupt putative autocrine driven leukemic cell growth could reestablish sensitivity to ATRA. Using the MTT cytotoxicity assay, comparison of ED50 values of suramin alone revealed HL-60 cells to be more resistant than HL60R (38.7 vs. 1 3.4,uM). Synergy or antagonism between combinations was then assessed using a combination-index CI-isobolo gram method. Combinations of suramin (3.5–56 $\mu$M) and ATRA (0.001–0.16 $\mu$M) at a ratio of 350:1 showed synergy with a mean CI value of 0.72+0.06 SD (0.61–0.79) with the HL-60 cell line. However with HL-60 R cells, these combinations were antagonistic with CI values of 1.40+0.21 (1.13–1.63) despite greater sensitivity to suramin alone. Combination studies with suramin and cytosine arabinoside were not synergistic with HL-60 cells, but did show additive activity. While suramin addition was not useful in restoring ATRA sensitivity, the combination was synergistic with ATRA sensitive HL-60 leukemic cells. In this human leukemia model, suramin in combination with the differentiating agent ATRA offers a novel treatment approach.

Methods

Cell lines chosen for this study include the ATRA sensitive human acute leukemia HL-60 and the ATRA resistant subclone, HL-60R. While originally described as an acute promyelocytic cell line, more recent work categorizes this line as an acute myelogenous leukemia. The sensitivity of these cell lines to ATRA and suramin alone as single agents has been assessed. These data permit the description of the IC50 concentrations for the individual agents. The assays of proliferation consist of cell proliferation after 3–5 days of exposure to the agents. Cell proliferation is assayed using a modification of the original MTT calorimetric assay described by Mossman, et al. In similar fashion, a dose response curve to cytosine arabinoside has been generated. Using the IC50 values for each agent alone allows selection of reasonable drug combinations. The data software program, "Dose effect analysis with microcomputers" (BioSoft, Inc.) developed by Dr. Chou, et al. is utilized. This computer analysis program allows the assessment of drug combinations for synergistic, additive, or antagonistic interactions.

Compounds related to vitamin A when used together with drugs that inhibit growth factor related tumor cell growth result in greatly increased activity against certain forms of leukemia. The compounds which are related to vitamin A are known as retinoids and the drug which inhibits growth factor related tumor cell growth is known as suramin. The inventors observe the growth of human leukemia cell lines in laboratory culture which were originally obtained from patients with diseases known as acute promyelocytic leukemia and acute myeloid leukemia to first discover the most useful combinations of retinoids plus suramin to inhibit the leukemia cell lines. Each of several retinoid compounds are tested in combination with suramin or a very potent analog, NF110. Leukemia cell lines which are resistant to retinoids are tested to see if they remain sensitive to the combination or are resistant also to the combination of retinoids with suramin. The most promising combinations are tested against fresh acute leukemia patient samples. All of the testing which has been done in laboratory culture are examined in an animal model system of human leukemia cell growth. Finally, possible mechanisms of why retinoids plus suramin have such greatly increased activities is studied.

The invention combines certain vitamin analogs (retinoids), when used in conjunction with anti-growth factor agents (suramin and analogs), and can result in synergistic activities against certain myeloid leukemias.

To define these activities, the rationale for such synergism, and preclinical models to examine the potential for anti-leukemic treatment include;

1. Utilizing in vitro human leukemia models, define the capacity for synergism between retinoids and suramin/ analogs and the most advantageous doses and sequencing.
   a.) Utilizing retinoic acid sensitive human leukemic cell lines (NB4) derived from an acute promyelocytic leukemia (APL) patient, examine the activity of all-trans retinoic acid (ATRA), 9-cis retinoic acid, and 13-cis retinoic acid in combination with suramin or its most potent analog (see section H), NF110.
   b) Utilizing a retinoic acid sensitive human myeloid leukemic cell line (HL60) derived from an acute myeloid leukemia (AML) patient, examine in like fashion the retinoids (as above) In combination with suramin/NF110.
   c) Examine in the above models if sequential therapy (retinoids followed by the addition of suramin, or the converse) is superior to simple combination therapy.
   d) Utilizing cell lines selected for retinoid resistance (NB4.306, HL-60R) examine if synergism with combination therapy is retained or abrogated.
   e) Take the most promising combination as defined above, and examine the in vitro activity against de novo acute myeloid leukemia patient samples.
2. Utilizing the SCID mouse host system, take the most promising agent combinations and examine the response of human leukemia cell lines in the SCID mouse hosts.
3. Investigate potential mechanisms of the ATRA/suramin synergistic activity as they relate to cytokine receptor availability on treated human leukemia cell lines.

Previous publications disclose a novel nucleotide binding site on murine and human granulocyte/macrophage-colony stimulating factor (GM-CSF) which is critical to the biologic activity of this cytokine. The inventors have subsequently shown that a pharmacologic antigrowth factor agent, suramin, interacts with the GM-CSF binding site and inhibits GM-CSF dependent cell growth.

Acute myeloid leukemic (AML) cells produce cytokines, possess their receptors, and in 70% of patients with AML have evidence of in vitro autonomous growth related to autocrine growth factor loops, particularly with GM-CSF (31) and IL-1 (42–45). The effect of suramin on HL-60 human leukemic cells was examined and inhibition resulted as has been previously noted (48). A graphical correlation was then generated which shows a very agreeable correlation as regards rank ordering of inhibition of both nucleotide binding and leukemia proliferation (Table 1). NF110 has been discovered to have a greatly enhanced activity (5–10 fold) against HL-60 and the HL-60R (trans retinoic acid resistant) cell line (FIG. 1).

TABLE 1

Inhibitory Potency of Suramin and Suramin Analogs:
Competition curves for nucleotide, photoprobe
incorporation into rhGM-CSF gave half-maximal
inhibitions of photoprobe incorporation as compared to
control. Similarly, cell proliferating of GM-CSF
dependent (Mo7E) and autonomously proliferation (GM-CSF
independent) human leukemia cells (HL-60) gave half-
maximal inhibition of growth. Results are expressed as
micromolar concentrations.

| Compound | Half-maximal inhibition of nucleotide binding | Half-maximal inhibition of Mo/7E growth (GM-CSF dependent) | Half-maximal inhibition of HL-60 growth (GM-CSF independent) |
|---|---|---|---|
| NF110 | 1.5 | 52 | 6 |
| suramin | 2.5 | 68 | 38 |
| NF302 | 2.0 | 76 | 80 |
| NF201 | 2.3 | 76 | 155 |
| NF023 | 5.0 | 102 | 175 |
| NF103 | 16.0 | 141 | not reached |

Suramin plus ATRA strongly inhibited HL-60 and HL-60R growth. The data software program, "Dose Effect Analysis with Microcomputers" (Biosoft, Inc.) (50–52) has analyzed a number of experiments utilizing combinations of ATRA and suramin. The analysis utilizing the software program now reveals that this activity is a truly synergistic one (FIG. 2).

Table 2 displays the fractional inhibition by each agent singly and in combination against HL-60. Single drug dose-effect relationship parameters (Dm, m, and r) were calculated for suramin (D1) and ATRA (D2).

TABLE 2

Example of experimental design and dose-effect
relationship of suramin and all-trans retionoic acid
(ATRA) and their combination on the growth of HL60
cells after 5 days exposure:
The parameters m, Dm, and r are the slope, antilog
of x-intercept, and the linear correlation coefficient
of the median-effect plot, which signifies the shape of
the dose-effect curve, the potency ($IC_{50}$), and
conformity of the data to the mass-action law, respectively.
Dm and m values are used for calculating the CI values.
CI < 1, CI = 1, and CI > 1 indicate synergism,
additivity, and antagonism, respectively. As based on the
classic isobologram equations, CI can be calculated by the
equation $CI = [(D)_1/(D_x)_1] + [(D)_2/(D_x)_2]$, where
$D_x = Dm[fa/1 - fa)]^1$, and where fa = fractional inhibition.
HL 60 Cells

| Suramin (μM) | ATRA (μM) | Fractional Inhibition | m | Dm | r | CI |
|---|---|---|---|---|---|---|
| 3.5 | | .020 | | | | |
| 7.0 | | .047 | | | | |
| 14.0 | | .093 | | | | |
| 28.0 | | .419 | | | | |
| 56.0 | | .678 | 1.725 | 38.6658 | .98606 | |
| | .001 | .561 | | | | |
| | .01 | .777 | | | | |
| | .02 | .790 | | | | |
| | .04 | .823 | | | | |
| | .08 | .826 | | | | |
| | .16 | .835 | .2729 | .00022 | .95094 | |
| $D_1 + D_2$ (350:1) | | | | | | |
| 3.5 | .01 | .764 | | | | .69631 |
| 7.0 | .02 | .806 | | | | .6175 |
| 14.0 | .04 | .831 | | | | .75907 |
| 28.0 | .08 | .867 | | | | .72063 |
| 56.0 | .16 | .897 | .3505 | .12781 | .996 | .78735 |

Figure 3:
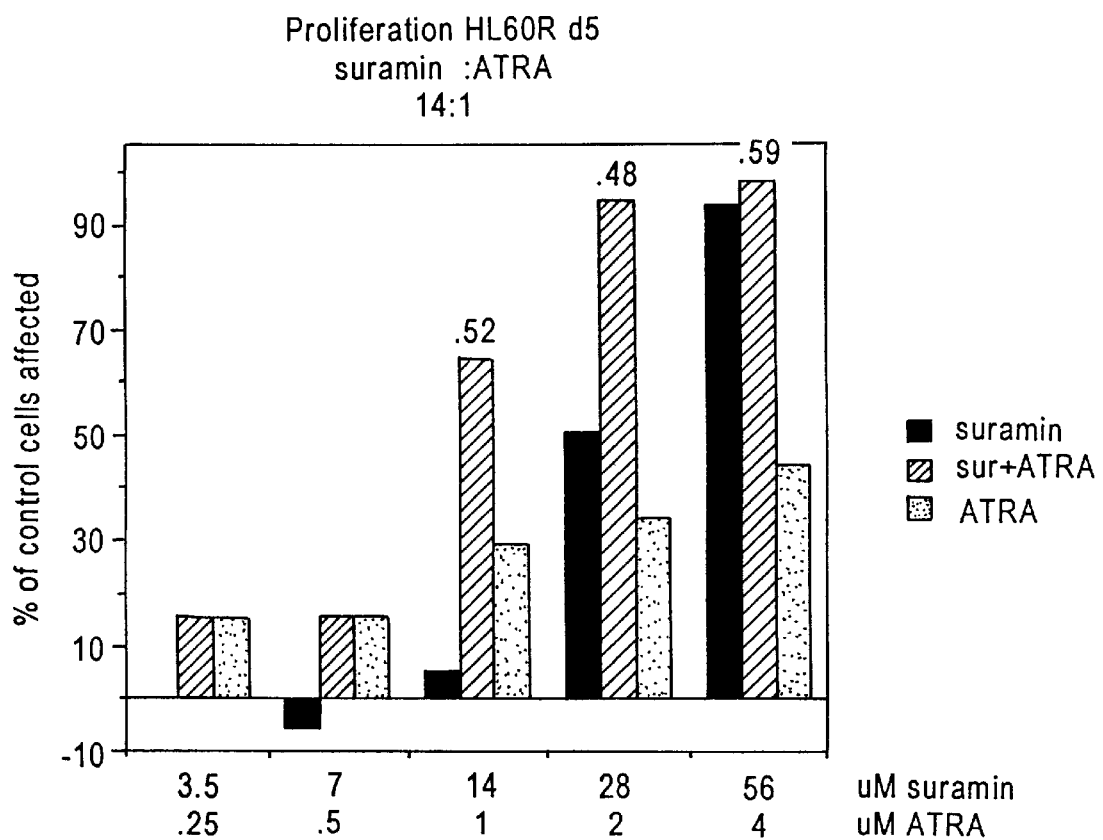
FIG. 3 shows ATRA plus suramin also inhibited HL-60R.

From studies of single drug, the dose ranges were selected to cover the concentrations above and below the IC-50 values of each agent. This led to the generation of the combination indices (CI) based on the classic isobologram equation. Results showed definite synergism (CI values less than 1) with the HL-60 cell line and this combination (Table 2, FIG. 2). ATRA plus suramin also inhibited HL-60R (FIG. 3), synergism was encountered only at the higher doses per the computer analysis.

Figure 4:
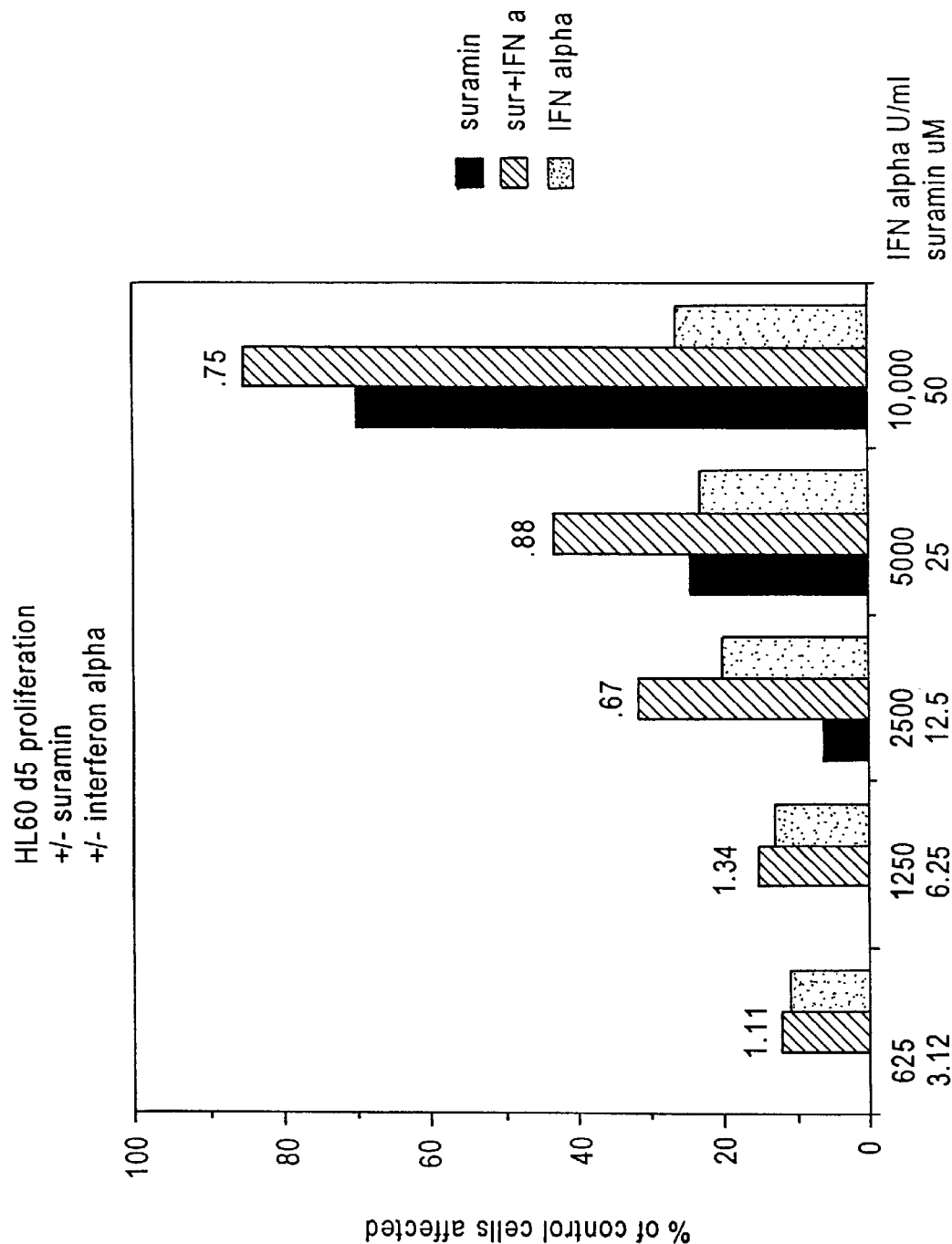
FIG. 4 shows alpha interferon given in combination with suramin inhibits the proliferation of HL-60 cells in a synergistic fashion.
Figure 5:
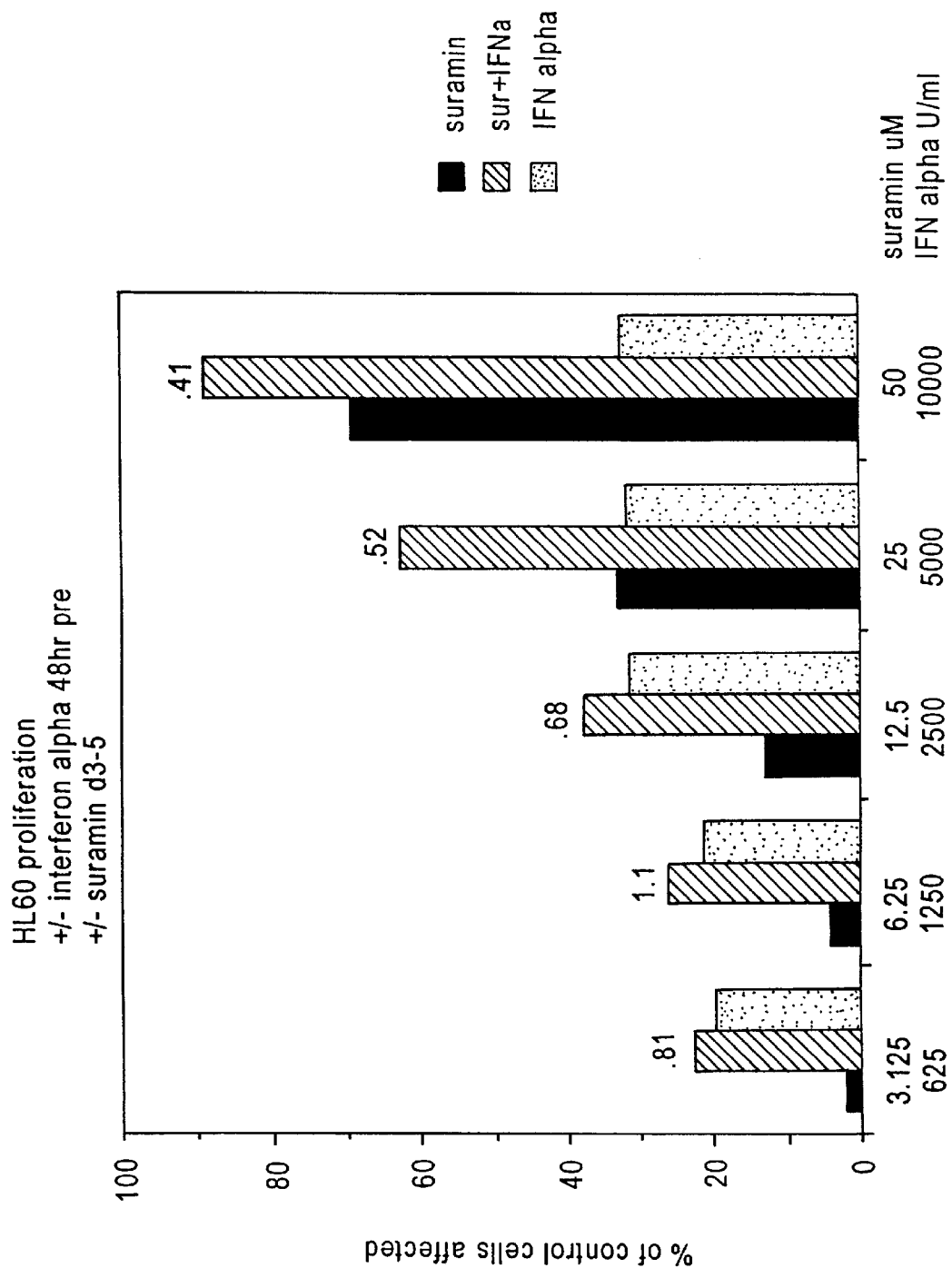
FIG. 5 shows interferon was given for the initial 48 hours of incubation followed by an additional 72 hours during which both interferon and suramin were present, the results were not only synergistic, but showed greater activity than the simple combination together.
Figure 6:
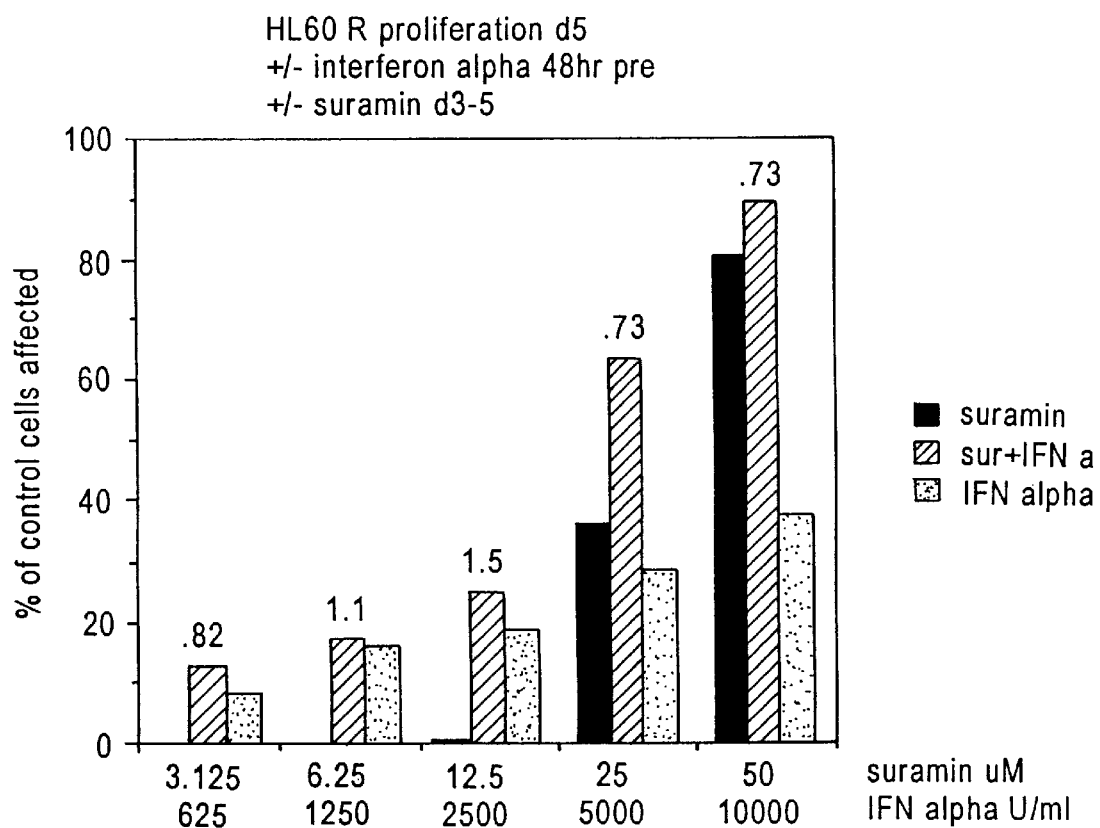
FIG. 6 shows synergism with the combination of α-interferon and suramin were also noted against the HL-60R cell line at doses greater than 25 mM suramin and 5,000 units/ml α-interferon.
Figure 7:
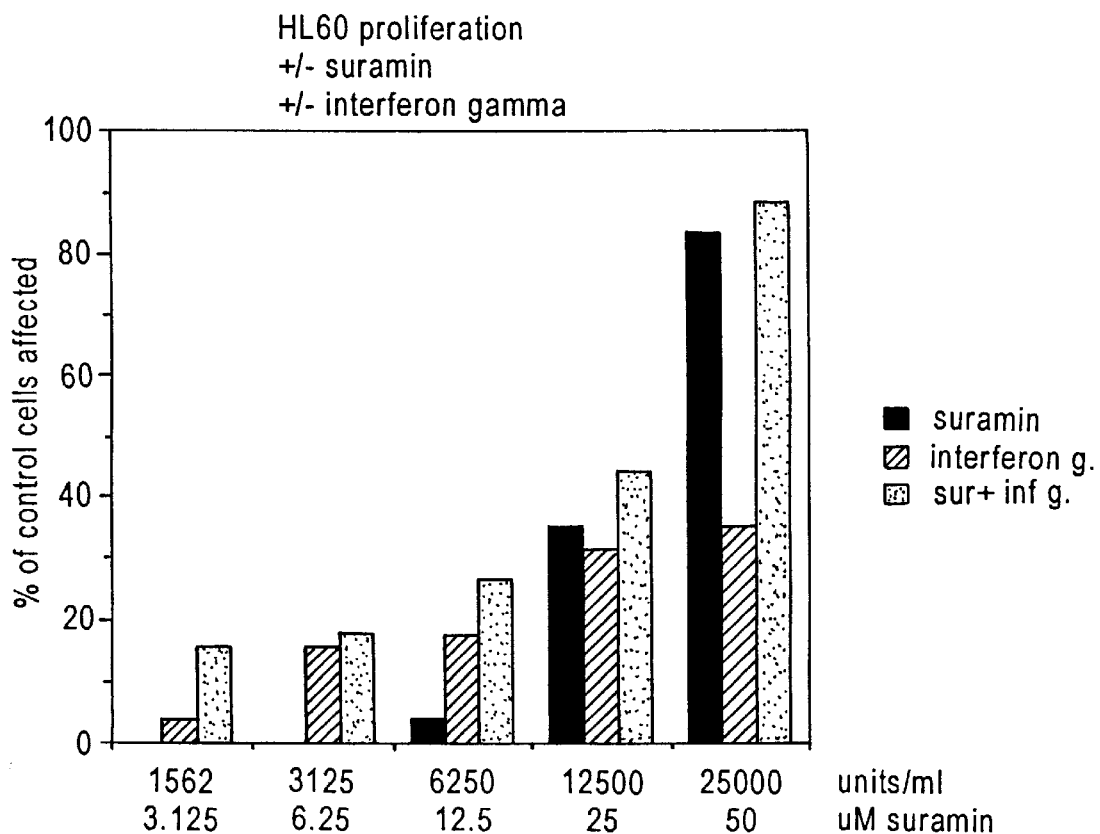
FIG. 7 shows the addition of suramin and interferon together for a 5-day incubation showed additive activity against HL-60.
Figure 8:
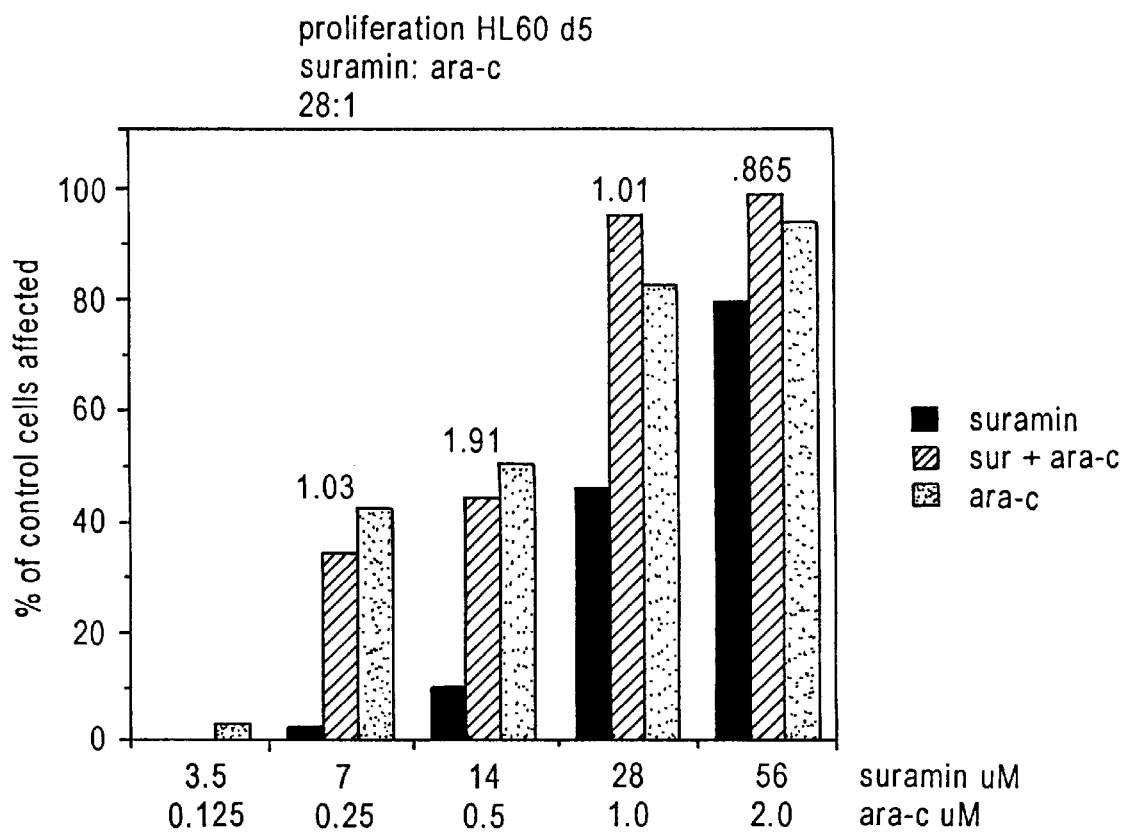
FIG. 8 shows additive activity against HL-60 for suramin and ARA-C.

In similar fashion, α-interfereon given in combination with suramin inhibits the proliferation of HL-60 cellls in a synergistic fashion (FIG. 4). In a related experiment, when interferon was given for the initial 48 hours of incubation followed by an additional 72 hours during which both interferon and suramin were present, the results were not only synergistic, but showed greater activity than the simeple combination together (FIG. 5). Synergism with the combination of α-interferon and suramin were also noted against the HL-60R cell line at doses greater than 25 mM suramin and 5,000 units/ml α-interferon (FIG. 6). Finally, the addition of suramin and interferon together for a 5-day incubation showed additive activity against HL-60 (FIG. 7), and for suramin and ARA-C (FIG. 8).

The capacity to perform the detailed dose-effect combination drug analyses which support our hypothesis regarding potential synergism of the suramin class agents with retinoid compounds.

Differentiation agents, specifically ATRA, are used in the treatment of acute promyelocytic leukemia (APL) and other retinoids are in clinical trials with other acute myeloid leukemias (7,8). The efficacy of ATRA to induce terminal differentiation (thus depleting the leukemic blast population) is proven; however, recrudescence of leukemia after a short period of complete remission is common and new autocrine growth factor loops have been proposed as one mechanism of resistance (1). Suramin has anti-growth factor activity against HL-60, a human acute leukemia cell line sensitive to ATRA (48). The possibility that agents with anti-growth factor activity can provide additive or synergistic effects upon ATRA sensitive and ATRA resistant leukemia cell lines was explored. The mainstay of therapy for acute leukemia remains chemotherapy. However, for adults, a 60–70% initial complete remission rate results in only 20–25% long-term survivorship (excepting APL with 60% long-term survivorship with ATRA plus chemotherapy). Alternatively, direct assessment of cells capable of forming colonies, colony forming unit, leukemia (CFU-L) are examined as a measure of cells capable of continued leukemic growth. Approximately 25 microliters of cell suspension are taken from each sample and plated in wells containing culture medium consisting of IMDM+10% FBS+(Difco). For colony assay, aggregates of at least 40 cells and clusters (4–39 cells) are scored after 12–14 days of culture. The number of CFU-L are expressed as the number of colonies derived from the original suspension culture (S5).

Finally, the results seen with leukemic cell lines are correlated with selected agents and combinations of agents, against de novo acute leukemia cells. Therapeutic apheresis results in the removal of large quantities of leukemia cells from patients presenting with a high degree of leukocytosis (generally blast count greater than 100,000/CC3). These large numbers of cells are frozen in liquid nitrogen with DMSO in the usual fashion in aliquots. This allows for repeated examinations from the same patient source and allow for some control regarding the reproducibility of results.

The procedures for measurement of inhibition of proliferation or the induction of differentiation, etc., are as described above for the leukemic cell lines noted. These techniques have been utilized in other studies and are well established in the literature (31).

As noted above, IC50 values for each agent alone are established for comparison purposes. The data software program, Dose effect analysis with microcomputers" (BioSoft, Inc.) (51) analyzed a number of experiments to date utilizing combinations of ATRA and suramin. This computer analysis program has been utilized to assess and has been validated by multiple laboratories (50–52).

Experiment 2:

Information derived from the prior experiments described above leads to examination of retinoids and anti-growth factor (suramin and NF110) agents alone and in combination utilizing a SCID mouse model of human leukemia proliferation.

Efficacy of therapeutic agents is a predictor of in vivo effects. A relevant animal model system exists for in vivo testing of agents and combinations of agents.

Methods

SCID mice weighing greater than 25 grams are utilized as host animals for human acute leukemia cell lines which have been established in in-vitro culture (56). 1×10 cells are injected either intravenously or subcutaneously as appropriate to the experiment. As 2 of the cell lines (NB4 and NB4.306) must be grown in SCID mice, the number of cells to be injected may vary and a cell dose compatible with leukemic cell engraftment are established for those cell lines separately.

Immune deficient SCID mice are utilized. Cells are inoculated into animals with minimal numbers of animals consisting of 5 per control/treatment group. The cell lines are inoculated either intravenously (56) or subcutaneously (57) at a dose of from $10^6$ to $10^8$ per animal as established for engraftment for the individual cell lines being utilized. Mice receiving intravenous inoculations are pre-treated one to two days prior to injection with 200 reds of sub-lethal irradiation to enhance marrow engraftment of the leukemic cell line as per published procedures (56). This sub-lethal dose may enhance acceptance of xenografts by diminishing any natural killer cell activity.

Subsequent to leukemic cell engraftment, treatment of the animals commences 1 week after leukemia cell injection. Treatment is daily for 5 days and dosages conform to ATRA work or derived from in vitro concentrations from the experiments above and pharmacokinetic information on suramin (58). ATRA is administered orally through a gavage needle. Suramin is administered by intravenous or intraperitoneal injection.

These mice are examined at least once and usually twice daily and premorbid signs such as hunching, lack of mobility, or other clear signs of animal distress result in the animal being sacrificed by cervical dislocation (59). Alternatively, the animals injected by the subcutaneous route have their tumors measured on a daily basis and when such tumors reach 1.5 centimeters in size, these animals are sacrificed (57).

Tissues are obtained at the time of animal sacrifice from representative animals include blood specimen for blood smear and assessment of leukemic cell growth, one femur from which bone marrow smears will be made and examined, and in the case of the subcutaneously injected animals, the resulting tumor are surgically excised and touch preps made and examined. The histologic examinations assure that the animal indeed did have engraftment of the human acute leukemia cell line and that it was responsible for the animal's death.

Outcomes of groups of animals per control or treatment group are used to derive mean+standard error of the mean as regards survival. In the case of subcutaneous leukemic cell injection, bidimensional tumor measurements (by calibers) on a set day post injection (defined by how well the individual lines engraft and grow) are compared similarly between groups. Comparison of treatment groups versus control are analyzed.

Experiment 3:

Potential mechanisms of ATRA/suramin synergistic activity are investigated as they relate to cytokine receptor density on treated human leukemia cells.

Data indicates synergism, i.e., supra-additive activity, of ATRA plus suramin. Synergism is often obtained when two agents are interfering with a common metabolic pathway. In this case, it is believe that ATRA may diminish GM-CSF receptors on the surface of leukemia cells in a fashion analogous to down regulation of IL-6 receptors (60) and TNF receptors (61) on myeloma and lymphoma cells, respectively. This theoretically potentiates the cytokine (GM-CSF)—receptor blockade which is believed to be a major mechanism of suramin activity.

Methods: Human leukemic cell lines (NB4, HL-60) are treated with a selected retinoid, suramin, or a combination for 8–24 hours. These cells are analyzed by flow analysis (FACs Scar, Becton Dickenson) for GM-CSF receptors after application of monoclonal antibodies directed against either GM-CSFRα or GM-CSFβ (Santa Cruz Biotech, Inc.) with labeled FITC/anti-mouse second antibody. These analyses are conducted by the Cancer Center's Flow Analysis Core Facility and follow previously published methodology. Results of treatment is compared to appropriately matched control samples. Testing of selected agents/combinations against fresh human leukemia samples to confirm cell line results is anticipated.

Comparisons of relative receptor density between treated and matched control samples are analyzed to ascertain statistical differences.

In conclusion:

1. Suramin is active against HL60 (as previously reported by others also) and is also active against HL-60R and NB4.

2. The combination of ATRA and suramin is synergistic against HL-60; this is found in the HL60R cells at higer ATRA concentrations tested.

3. The combination of suramin and Ara-C is additive using this methodology, as well as γ interferon and suramin.
4. Synergism between suramin and ATRA is believed to relates to their mode of action. Suramin interacts with cytokines and thus may interrupt autocrine growth factor loops which have been described for acute leukemia. ATRA, along with its activity in the nucleus, results in the reduction of cytokine receptors. It is believed that both of these agents are therefore interacting against autocrine signal transduction pathways, one by interfering with cytokine-receptor interaction and the other, by down modulating the number of receptors available.
5. The combination of suramin and α-interferon is synergistic.

PHARMACEUTICAL EXAMPLE

Further, the composition of the present invention is useful in pharmaceutical formulation for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compositions of the invention. The compositions are useful in pharmaceutical compositions (wt %) of the active ingredient with a carrier or vehicle in the composition in about 1 to 20% and preferably about 5 to 15%.

Either fluid or solid unit dosage forms can be readily prepared for oral administration. For example, the composition of the invention can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixers may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixer.

Pharmaceutical compositions for parenteral and suppository administration can also be obtained using techniques standard in the art.

The above parenteral solutions or suspensions may be administered transdermally and, if desired a more concentrated slow release form may be administered. Accordingly, incorporation of the active compounds in a slow release matrix may be implemented for administering transdermally. The compounds may be administered transdermally at about 1 to 20% of the composition and preferably about 5 to 15% wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, avoiding gastrointestinal incompatibilities and providing a predictable and extended duration of activity. However, the main function of the skin is to act as a barrier to entering compounds. As a consequence, transdermal therapy has so far been restricted to a limited number of drugs that possess the desirable physicochemical properties for diffusion across the skin barrier. One effective method of overcoming the barrier function of the skin is to include a penetration enhancer in the formulation of a transdermal therapeutic system. See Barry, Brian W.: *Dermatological Formulations: Percutaneous Absorption* (Dekker, New York, 1983); Bronough et al, *Percutaneous Absorption, Mechanisms-Methodology-Drug Delivery,* (Marcel Dekker, New York, NY 1985); and Monkhouse et al, Transdermal drug deliver-problems and promises. *Drug Dev. Ind. Pharm.,* 14, 183–209 (1988).

A penetration enhancer is a chemical compound that, when included in a formulation, temporarily increases the permeability of the skin to a drug allowing more of the drug to be absorbed in a shorter period of time. Several different types of penetration enhancers have been reported such as dimethylsulfoxide, n-decyl methyl sulfoxide, N,N-dimethylacetamide, N<Ni-dimethylformamide, 1-dodecylazacycloheptan-2-one (Azone), propylene glycol, ethanol, pyrrolidones such as N-methyl-2-pyrrrolidone (NMP) and surfactants. See Bronough et al, supra, and Stoughton et al, Azone: a New Non-toxic enhancer of percutaneous penetration. *Drug Dev. Inc. Pharm.,* 9, 725–744 (1983).

N-methyl-2-pyrrolidone is a versatile solvent which is miscible with water, ethyl alcohol, ether, chloroform, benzene, ethyl acetate and carbon disulfide. N-methylpyrrolidone has been widely used as a solvent in industrial processes such as petroleum refining, GAF Corp.: "M-Pyrol (N-methyl-2-pyrrolidone) Handbook.", GAF Corp., New York, 1972. It is currently used as a solubilizing agent in topical and parenteral veterinary pharmaceuticals and is now under consideration for use in products intended for humans, Wells, D. A. et al: Disposition and Metabolism of Double-Labeled [$^3$H and $^{14}$C] N-methyl-2-pyrrolidone in the Rat. *Drug Met. Disps.,* 16, 243–249 (1988). Animal and human experiments have shown very little irritation or sensitization potential. Ames type assays and chronic exposure studies have not revealed any significant toxicity, Wells et al, Mutagenicity and Cytotoxicity of N-methyl-2-p[yrrolidone and 4-(methyl amino) Butanoic Acid in the Salmonella/microsome Assay. *J. Appl. Tox.,* 8, 135–139 (1988). N-methylpyrrolidone has also been shown to be an effective penetration enhancer. Barry et al, Optimization and Bioavailability of Topical Steroids: Penetration Enhancers Under Occlusion. *J. Inv. Derm.,* 82, 49–52 (1984); Effect of Dose Variation, Deposited Drug Films, Occlusion and the Penetration Enhancer N-methyl-2-pyrrolidone. *J. Pharm. Pharmacol.,* 37, 27–37 (1984); Holegaard et al, Vesical Effect on Topical Drug Delivery IV. Effect of N-methylpyrrolidone and Polar Lipids on Percutaneous Transport. *Int. J. Pharm.*, 43, 233–240 (1988); Sugibayashi et al, Effect of Several Penetration Enhancers on the Percutaneous Absorption of Indomethacin in Hairless Rat. *Chem. Pharm. Bull.*, 36, 1519–1529 (1988); Bennett et al, Optimization of Bioavailability of Topical Steroids: Non-occluded penetration Enhancers Under Thermodynamic Control. *J. Pharm. Pharmacol.*, 37, 298–304 (1985); Sasaki et al, Enhancing Effect of Pyrrolidone Derivatives on Transderman Drug Delivery. 1. *Ing. J. Pharm.*, 44, 14–24 (1988); lee et al, Toxicity of N-methyl-2-pyrrolidone (NMP): Tetratogenic, Subchronic and Two-year Inhalation Studies, *Fund. Appl., Tox.*, 9, 222–235 (1987).

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 45mg/$M^2$/d/po for ATRA, 200–1100 mg $M^2$/d/iv; and 3–10 million units/d subcutaneous for α-interferon daily, or preferably about three times per week.

REFERENCES

1. Rubertea E, Kastner P, Dolle P, Krust A, Leroy P, Mendelsohn C, et al. Retinoic acid receptors in the embryo. Semin Dev Biol 2:153–9, 1991.
2. DeLuca L, Retinoids and their receptors in differentiation, embryogenesis and neoplasia. FASEB J 5:2924–33, 1991.
3. Frankel S R, Warrell R P. Retinoids in leukemia and myelodysplastic syndromes. In: Hong W k, Lotan R. (eds.) Retinoids in Oncology. New York. Marcel, Dekker. pp. 147–78, 1993.
4. Degos L Dombret H, Chornienne C, Daniel M-T, Micler J-M, Chastang C, Castaigne S, Fenaux P. All-trans-retinoic acid as a differentiating agent in the treatment of acute promyelocytic leukemia. Blood 85:2643–53, 1995.
5. Tobler A, Dawson M I, and Koeffler H P. Structure-function relationship in normal and leukemic hematopoIesis in vitro. J Clin Invest 78:303–309, 1986.
6. Personal Communication, K. Kopecky and F. Appelbaum 1995. Please Note: Dr. Doukas (PI) is a member of the South West Oncology Group Leukemia and Leukemia Biology Committees.
7. Early E. and Dmitrovsky E. Acute promyelocytic leukemia: Retinoic acid response and resistance. J Investig Med 43:337–344, 1995.
8. Warrell R P, de The, H, Wang Z-Y, and Degos L Review Article. Acute promyelocytic leukemia. NEJM 329(3): 177–189, 1993 (July 15).
9. Muindi J, Frankel S R, Miller W H Jr. Continuous treatment with all-trans retinoic acid causes a progressive reduction in plasma drug concentrations: implications for relapse and retinoid "resistance" in patients with acute promyelocytic leukemia. Blood 79:299–303, 1992.
10. Comic M, Delva L Guidez F, Balitrand N, Degos L Chomienne C. Induction of retinoic acid-binding protein in normal and malignant human myeloid cells by retinoic acid in acute promyelocytic leukemia patients. Cancer Res 52:3329–34, 1992.
11. Gold E J, Mertelsman L M, Itri T, Gee Z, Arlin S, Kempin B, Clarkson B, Moore M A S. Phase I clinical trial of 13-cis retinoic acid in myelodysplastic syndromes. Cancer Treat Rep 67:981–986, 1983.
12. Aul C, Runde V, Gatterman N. All-trans retinoic acid in patients with myelodysplastic syndromes: results of a pilot study. Blood 82:2967-,4, 1993.
13. Eisenhauer E A, Lippman S M, Kavanagh J J, Parades-Espinoza M, Arnold A, Hong W K, Massimini G, Schleuniger U, Bollag W, Holdener E E, and Krakoff I. Combination 13-cis-retinoic acid and interferon-α in the therapy of solid tumors. Leukemia 8(Sup 3):S38–S41, 1994.
14. Lippman Sm, Kavanagh J J, Paredes-Espinoza M. Delgadillo-Madrueno F, ParedesCasillas P, Hong Wk, Holdener E, Krakoff I H. 13-cis-retinoic acid plus interferon-α 2a: Highly active systemic therapy for squamous cell carcinoma of the cervix. J Natl Cancer Inst 84:241–245, 1992.
15. Grant S, Bhalla K, Weinstein B, Pestka S, Mileno M D, and Fisher P B. Recombinant human interferon sensitizes resistant myeloid leukemic cells to induction of terminal differentiation. Biochem and Biophys Res Commun 130 (1):379–388, 1985.
16. Taetle R, Dos Santos B, Akamatsu K, Koishihara Y, and Ohsuagi Y. Effects of alltrans retinoic acid and anti-growth factor receptor antibodies on growth and programmed cell death of human myeloma cells. Blood 86:743A, 1995.
17. Dubois C, Schlageter M H, de Gentile: Hematopoietic growth factor expression and ATRA sensitivity in acute promyelocytic blast cells. Blood 83:3264–3270, 1994.
18. Metcalfe, D. The molecular biology and functions of the granulocyte-macrophage colony-stimulating factors. Blood 67:257–267, 1986.
19. Metcalfe D., Begley C G., Johnson G R: Biologic properties in vitro of a recombinant human granulocyte-macrophage colony-stimulating factor. Blood 67:37–45, 1986.
20. Campbell S., Kim H., Doukas M A, Haley BE.: Photoaffinity labeling of ATP and NAD+binding sites on recombinant human interleukin-2. Proc Natl Acad Sci 87:1243–1246, 1990.
21. Heistand D M. Dissertation "A Study of the Nucleotide Binding Properties of Interleukin-lB and Tumor Necrosis Factor-a." Director: Dr. Boyd Haley. The Graduate School, University of Kentucky, 1994.
22. Chavan A J, Haley B E Interaction of nucleotides with acidic fibroblast growth factor (FGF-1). Biochem 33:7193–7202, 1994.
23. Doukas M A, Chavan A J, Gass C, Boone T, and Haley B E: Identification and description of a nucleotide binding site on recombinant murine granulocyte/macrophage-colony stimulating factor. Bioconj Chem 3:484–492, 1992.

24. Doukas M. A., Chavan A., Gass C., Boone T., & Haley B. E.: Inhibition of GM-CSF Activity by Suramin and Suramin Analogs is Correlated to interaction with the GM-CSF Nucleotide Binding Site. Cancer Research 55:5161–5163, 1995.
25. Borken, J. The Crime and Punishment of I. G. Farben, p5. New York: The Free Press, 1978.
26. Heymann B, Angew: Uber Chemotherapevtisch wirksame organische verbindungen, insbesondere UBayer 205n. Chem.32:585–589, 1924.
27. Hawking, F: Suramin: with special reference to onchocerciasis. Adv. Pharmacol. Chemother. 15:289–322. 1978.
28. Stein, C: Suramin: a novel antineoplastic agent with multiple potential mechanisms of action. Canc Res 53:2239–2248, 1993.
29. Pech N, Hennine O, Goldwasser E: Further study of internal autocrine regulation of multipotent hematopoietic cells. Blood 82:1502–1506, 1993.
30. Freedman M H, Grunberger T, Correa P, Axelrad A A, Dube I D, Cohen A: Autocrine and paracrine growth control by granulocyte-monocyte colony-stimulating factor of acute lymphoblastic leukemia cells. Blood 81:3068–3075, 1993.
31. Rogers S Y, Bradbury D, Kozlowski R, Russell N H: Evidence for internal autocrine regulation of growth in acute myeloblastic leukemia cells. Exper Hernatol 22:593–598, 1994.
32. Strassman G, Fong M, Freter C E: Suramin interferes with IL-6 receptor binding I vitro and inhibits colon-26-mediated experimental cancer cachexia in vivo. J Clin Invest 92:2152–2159, 1993.
33. Mills G B, Zhang N, May C, Hill M, Chung A: Suramin prevents binding of 1L-2 to its cell surface receptor: a possible mechanism for immunosuppression. Canc Res 50:30363042, 1990.
34. Alzoni R, Corti A, Grazioli L Surarnin induces deoligomerization of human tumor neaosis factor alpha. J Biol Chem 268:12526–12529, 1993.
35. Middaugh C R, Mach H, Burke C J: Nature of the interaction of growth factors with suramin. Biochem 31:9016–9024, 1992.
36. Jindal H. K, Anderson C. W., Davis R. G., and Vishwanattha J. K.: Suramin effects DNA synthesis in HeLa cells by inhibition of DNA polymerases. Cancer Res., 50:7754–7757, 1 990.
37. Bojanowski K, Lelievre S., Markovits J., Couprie J., Jacqupmin-sablon, and Larsen A. K.: Suramin is an inhibitor of DNA topoisomerase in vitro and in chinese hamster fibrosarcoma cells. Proc. Natl. Acad. Sci. USA, 89:3025–3029, 1992.
38. Barret J. M., Ernould A. P., Rouillon M. H., Ferry G., Genton A., and Boutin J A.: Studies of the potency of protein kinase inhibitors on ATPase activities. Che_Biol. Interact. 86:17–27, 1993.
39. Hensey C. E, Bosboinik D., and Azzi A.: Suramin, an anticancer drug, inhibits protein kinase C and induces differentiadon in neuroblastoma cell cl one NB 2A. FEBS Lett. 258:156–158, 1989.
40. Kopp R, and Pfeiffer A.: Suramin alters phosphoinositide synthesis and inhibits growth factor receptor binding in HT-29 cells. Cancer Res., 50:6490–6496, 1990.
41. Sartor, O, McLellan, C A, Myers, C E, Borner, M M: Suramin rapidly alters cellular tyrosine phosphorylation in prostate cancer cell lines. J Clin Invest 90:2166–2174, 1992.
42. Estrov Z, Kurzrock R, Wetzler M, KantarJian H, Blake M, Harris D, Gutterman J U, Talpaz M. Suppression of chronic myelogenous leukemia colony growth by interleukin-1 (IL-1) receptor antagonist and soluble IL-1 recpetors: a novel application for inhibitors of activity. Blood 78:1476–1484,1991.
43. Estrov Z, Kurzock R, Estey E, Wetzler M, Ferrajoli A, Harris D, Blake M, Gutterman J U, Talpaz M. Inhibition of acute myelogenous leukemia blast proliferation by interleukin-1 (IL-1) receptor antagonist and soluble IL-1 receptors. Blood 79:1938–1945, 1992.
44. Strassmann G, D'Alessandro F, Fong M, Nordan R P, Nickel P, Chizzonite R. Surarnin blocks the binding of interleukin-1 to its receptor and neutralizes IL-1 biological activities. Int J Immunopharmac 16:921–939,1994.
45. Estrov Z, Talpaz M, Estey E H, Strassmann G. Role of suramin as an IL-1 inhibitor in suppresison of acute myelogenous leukemia progenitor proliferation. Exper Hematol 23:1080–1087, 1995.
46. LaRocca R V, Cooper M R, Stein C A: A pilot study of suramin in the treatment of progressive refractory follicular lymphomas. Ann Oncol 3:571–573, 1992.
47. Tefferi A, Silverstein M N, Plurnhoff E A: Suramin toxicity and efficacy in agnogenic myeloid metaplasia. J Natl Canc Instit 85:1520–1522, 1993.
48. Bai L, Nacmoto Y, Miyazaki M. Orita K, and Numba M: Antiproliferative Effects of Surarnin on Human Cancer Cells In Vitro and In Vivo. Acta Med Okayama 46(6):457–463, 1992.
49. Orchard P J, McIvor R S, Singh H A, Blazar B R. GM-CSF-induced internal autocrine proliferation occurs in a compartment outside of the endoplasmic reticulum. Exper Hematol 23:573–582, 1995.
50. Chou T C, Motzer R J, Tong Y, Bosl G J: Computerized Quantitation of Synergism and Antagonism of Taxol, Topotecan, a Rational Approach to Clinical Protocol Design. J Nat'l Can Inst 86(20):1517–1524. 1994.
51. Chou T C, Talalay P: Quantitative analysis of dose-effect relationships: the combined effects of multiple drugs or enzyme inhibitors. Adv Enzyme Regul 22:2755, 1984.
52. Chang T T, Gulati S C, Chou T C, Vega R, Gandola V L Ezzat Ibrahim S M, Yopp J, Colvin M, and Clarkson B D: Synergistic Effect of 4-Hydroperoxycyclophosph~mide and Etoposide on a Human Promyelocytic LeukPmia Cell Line (HL-60) Demonstrated by Computer Analysis. Cancer Research 45:2434–2439, 1985.
53. Mosmann' T. Rapid calorimetric assay for cellular growth and survival: Application to proliferation and cytotoxicity assays. J. Immunol. Meth, 65:55–63, 1983.
54. Breitman T R, Selonick S E, Collins S J: induction of differentiation of the human promyelocytic leukemia cell line (HL-60) by retinoic acid. Proc Natl Acad Sci 77:2936–2940, 1980.
55. Nakae, H and Asada, S: Synergistic Antiproliferative Effect of Interferons and Azidothymidine on HL60 Cells. Chem Pharm Bull. 40(3):821–822, 1992.
56. DeLord C, Clutterbuck R, Titley J.: Growth of primary human acute leukemia in SCID mice. Exp Hematol 19:991–993, 1991.
57. Pirrucello S J, Jackson J D, Lang M S: OMA-AML-1: A leukemic myeloid cell line with CD34+progenitor and CD15+spontaneously differentiating cell compartments. Blood 80:1026–1032, 1992.
58. Namikawa R, Ueda R, Kyoizluni S: Growth of human myeloid leukemias in the human marrow environment of SCID-hu mice. Blood 82:2S26–2536.
59. Beran M, Piza P, O'Brien S.: Biologic properties and growth in SCID mice of a new myelogenous leukemia cell line (KBM-5) derived from chronic myelogenous leukemia cells in the blastic phase. Canc. Res. 53:3603–3610, 1993.

60. Ogata A, Nishimoto N, Shima Y, Yoshizaki K, and Kishimoto T. Inhibitory effect of all-trans retinoic acid on the growth of freshly isolated myeloma cells via interference with interleukin-6 signal transduction. Blood 84(9): 304–3046, 1994 (November 1).

61. Totpal K, Chaturvedi M M, IaPushin R, and Aggarwal B B. Retinoids downregulate both p60 and p80 forms of tumor necrosis factor receptors in human histiocytic lymphoma U937 cells. Blood 85(12):3547–3555,1995 (June 15).

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

What is claimed is:

1. A method of treating leukemia comprising administering a synergistic composition comprising suramin and all-trans retinoic acid (ATRA) at a ratio of about 14:1 to about 3500:1.

2. The method according to claim 1, wherein the amount of suramin is at least about 3.5 $\mu$M, and all-trans retinoic acid (ATRA) is at least about 0.002 $\mu$M.

3. The method according to claim 2, wherein the amount of suramin is at least about 7 $\mu$M, and all-trans retinoic acid (ATRA) is at least about 0.002 $\mu$M.

4. The method according to claim 3, wherein the amount of suramin is at least about 14 $\mu$M, and all-trans retinoic acid (ATRA) is at least about 0.004 $\mu$M.

5. The method according to claim 2, wherein the amount of suramin is in a range of about 3.5 to about 56 $\mu$M, and the amount of all-trans retinoic acid (ATRA) is in a range of about 0.001 to 4 $\mu$M.

6. The method according to claim 5, wherein the amount of suramin is in a range of about 7 to about 56 $\mu$M, and the amount of all-trans retinoic acid (ATRA) is in a range of about 0.002 to about 4 $\mu$M.

7. The method according to claim 1, wherein the ratio is about 350:1.

8. A synergistic pharmaceutical composition for treating leukemia comprising suramin and all-trans retinoic acid (ATRA) at a ratio of about 14:1 to about 3500:1.

9. The pharmaceutical composition according to claim 8, wherein the amount of suramin is at least about 3.5 $\mu$M, and all-trans retinoic acid (ATRA) is at least about 0.002 $\mu$M.

10. The pharmaceutical composition according to claim 9, wherein the amount of suramin is at least about 7 $\mu$M, and all-trans retinoic acid (ATRA) is at least about 0.002 $\mu$M.

11. The pharmaceutical composition according to claim 10, wherein the amount of suramin is at least about 14 $\mu$M and all-trans retinoic acid (ATRA) is at least about 0.004 $\mu$M.

12. The pharmaceutical composition according to claim 9, wherein the amount of suramin is in a range of about 3.5 to about 56 $\mu$M, and the amount of all-trans retinoic acid (ATRA) is in a range of about 0.001 to 4 $\mu$M.

13. The pharmaceutical composition according to claim 12, wherein the amount of suramin is in a range of about 7 to about 56 $\mu$M, and the amount of all-trans retinoic acid (ATRA) is in a range of about 0.002 to about 4 $\mu$M.

14. The pharmaceutical composition according to claim 8, wherein the ratio is about 350:1.

* * * * *